US00PP32191P2

(12) United States Plant Patent
Zaiger et al.

(10) Patent No.: US PP32,191 P2
(45) Date of Patent: Sep. 15, 2020

(54) PEACH TREE NAMED 'LADY ERIN'

(50) Latin Name: *Prunus persica*
Varietal Denomination: Lady Erin

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/602,688

(22) Filed: Nov. 20, 2019

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./194, 197
See application file for complete search history.

*Primary Examiner* — Susan McCormick Ewoldt

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Clingstone fruit with firm, yellow flesh.
4. Fruit having an attractive red skin color.
5. Fruit with good flavor and eating quality.

1 Drawing Sheet

Botanical designation: *Prunus persica.*
Variety denomination: 'LADY ERIN'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach trees, which are known to us, and mentioned herein, 'Summer Amelia' Peach (U.S. Plant Pat. No. 24,777), 'Sunnirich' Peach (U.S. Plant Pat. No. 21,567) and the proprietary non-patented peach seedlings '56B472', '155LT581' and '162LX30'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from a first generation cross between our proprietary non-patented peach seedling '56B472' and 'Summer Amelia' Peach (U.S. Plant Pat. No. 24,777). The seed parent (56B472) originated as a first generation cross between our proprietary non-patented peach seedling selections '155LT581' and '162LX30'. A large number of these first generation seedlings were planted and grown on their own root system, during which time we recognized the desirable tree and fruit characteristics of the present seedling and selected it in 2014 for additional asexual propagation and commercialization.

ASEXUAL REPRODUCTION OF THE VARIETY

In 2014 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of very large size, yellow flesh, clingstone fruit with good flavor and eating quality. The fruit is further characterized by having firm flesh and attractive red skin color. In comparison to its proprietary non-patented peach seed parent '56B472' the fruit of the new variety is clingstone compared to freestone and is approximately 5 days earlier in maturity. In comparison to its pollen parent 'Summer Amelia' Peach (U.S. Plant Pat.

No. 24,777) the fruit of the new variety is larger in size and is approximately 23 days earlier in maturity. In comparison to the commercial variety 'Sunnirich' Peach (U.S. Plant Pat. No. 21,567) the fruit of the new variety has a higher degree of Brix and is approximately 20 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 700 hours at or below 45° F.

Trunk:

*Size*.—Medium, average circumference 57.2 cm at 22.9 cm above ground on a 5 year old tree.

*Stocky*.—Medium stocky.

*Texture*.—Medium shaggy, increases with age.

*Color*.—10YR 2/2.

Branches:

*Size*.—Medium. Average circumference 10.9 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 35 in a 25.8 square cm area. Average length 3.3 mm. Average width 1.8 mm. Color 10YR 5/6.

*Color*.—New growth 2.5GY 6/8. Mature growth varies from 10YR 3/4 to 10YR 3/6, varies with age of growth.

Leaves:

*Size*.—Medium. Average length 141.5 mm. Average width 32.5 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 13.5 mm. Average width 1.9 mm. Longitudinally grooved. Surface — glabrous. Color varies from 10Y 6/6 to 2.5GY 6/6.

*Glands*.—Type — reniform. Size — small. Average length 1.0 mm. Average diameter 0.9 mm. Number varies from 1 to 3, average number 2. Located primarily on the base of leaf blade and upper portion of petiole. Color 2.5GY 6/6.

*Stipules*.—None present at time of measurement.

*Color*.—Upper surface varies from 2.5GY 3/4 to 5GY 4/6. Lower surface varies from 5GY 5/4 to 5GY 4/4. Midvein color varies from 2.5GY 8/4 to 5GY 7/4.

Flower buds:

*Size*.—Large. Average length 90.6 mm. Average diameter 10.6 mm.

*Hardiness*.—Hardy with respect to California winters.

*Density*.—Dense.

*Form*.—Elongated.

*Pedicel*.—Average length 3.7 mm. Average width 1.1 mm. Surface- glabrous. Color varies from 2.5GY 6/8 to 5GY 6/6.

*Color*.—Varies from 7.5RP 6/12 to 7.5RP 8/6.

Flowers:

*Blooming period*.—Date of First Bloom Feb. 17, 2019. Date of Petal Fall Feb. 27, 2019, varies slightly with climatic conditions.

*Size*.—Large. Average height 20.3 mm. Average diameter 47.2 mm.

*Petals*.—Normally five, alternately arranged to sepals. Size — large. Average height 23.8 mm. Average diameter 20.1 mm. Petal apex — rounded. Petal base — truncate. Form — rounded to obovate. Arrangement — overlapping. Margin — sinuate. Color varies from 5RP 8/4 to 5RP 8/6, fades with age of flower.

*Sepals*.—Normally five, alternately arranged to petals. Size — large. Average length 6.1 mm. Average width 5.8 mm. Sepal apex — rounded to triangular. Shape — triangular. Margin — entire. Surface — upper surface glabrous, lower surface pubescent. Color — upper surface varies from 2.5GY 5/8 to 5GY 5/8. Lower surface varies from 5R 2/4 to 7.5R 2/6.

*Stamens*.—Average number per flower 42. Average filament length 15.7 mm. On average, the stamens are above the height of the petals. Filament color varies from N 9.5/(white) to 5RP 7/6. Anther color varies from 5Y 8/8 to 7.5R 3/10.

*Pollen*.—Self fertile. Color varies from 2.5Y 7/10 to 5Y 7/12.

*Pistil*.—Number — normally one. Average length 17.4 mm. Position of stigma an average of 2.4 mm below anthers. Surface — pubescent. Color varies from 7.5Y 8.5/6 to 10Y 8.5/6.

*Fragrance*.—Wanting.

*Color*.—Varies from 5RP 9/2 to 5RP 8/4.

*Pedicel*.—Average length 3.7 mm. Average width 1.2 mm. Color varies from 2.5GY 6/8 to 5GY 6/6.

*Number flowers per flower bud*.—Normally one.

Fruit:

*Maturity when described*.—Firm ripe and ready for consumption.

*Date of first picking*.—Jul. 21, 2019.

*Date of last picking*.—Jul. 31, 2019, varies slightly with climatic conditions.

*Size*.—Very large. Average diameter axially 83.3 mm. Average transversely in suture plane 93.9 mm. Average weight 391.0 grams, varies slightly with fertility of the soil, amount of thinning and climatic conditions.

*Form*.—Globose.

*Suture*.—Slightly lipped.

*Ventral surface*.—Slightly lipped.

*Apex*.—Rounded to slight tip.

*Base*.—Slightly retuse.

*Stem cavity*.—Rounded to slightly elongated in suture plane. Average depth 16.5 mm. Average diameter 13.2 mm.

Stem:

*Size*.—Small. Average length 8.7 mm. Average diameter 3.9 mm.

*Color*.—Varies from 10Y 7/8 to 10Y 7/6.

Flesh:

*Ripens*.—Evenly.

*Texture*.—Firm, meaty.

*Fibers*.—Few, small, tender.

*Firmness*.—Good, comparable to other commercial peach varieties.

*Aroma*.—Slight.

*Amydgalin*.—Undetected.

*Eating quality*.—Good.

*Flavor*.—Good, mild flavor, with a good balance between acid and sugar.

*Juice*.—Heavy amount, enhances flavor.

*Acidity*.—Not available.

*Brix*.—Average Brix 13.1°, varies slightly with amount of fruit per tree and climatic conditions.

*Color*.—Varies from 10YR 8/8 to 2.5Y 8.5/8 with 2.5R 4/10 anthrocyanin color bleeding into the flesh.

*Pit cavity*.—Average length 38.9 mm. Average width 29.9 mm. Average depth 12.4 mm. Color varies from 2.5R 2/2 to 2.5R 3/8.

Skin:

*Thickness*.—Medium.

*Surface*.—Smooth.

*Pubescence*.—Moderate amount, short in length.

*Tendency to crack*.—None.

*Color*.—Ground color varies from 2.5Y 8.5/8 to 2.5Y 8/10. Overspread with 2.5R 3/8 to 5R 4/8.

Stone:

*Type*.—Clingstone, medium adherence to flesh.

*Size*.—Large. Average length 37.9 mm. Average width 28.9 mm. Average thickness 22.8 mm.

*Form*.—Ovoid.

*Base*.—Flat.

*Apex*.—Pointed. Average length 2.7 mm.

*Surface*.—Pitted throughout, pits vary from round to elongated.

*Sides*.—Unequal, one side extending further from suture plane.

*Ridges*.—Relatively smooth, narrow ridges extending from base toward apex.

*Tendency to split*.—None.

*Color*.—Varies from 7.5R 3/4 to 7.5R 2/6 when dry.

Kernel:

*Size*.—Large. Average length 18.6 mm. Average width 12.7 mm. Average depth 6.4 mm.

*Form*.—Ovate.

*Viability*.—Viable, complete embryo development.

*Skin color*.—Varies from 2.5Y 8/10 to 2.5Y 8/8.

Use: Dessert.

*Market*.—Local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Cali., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

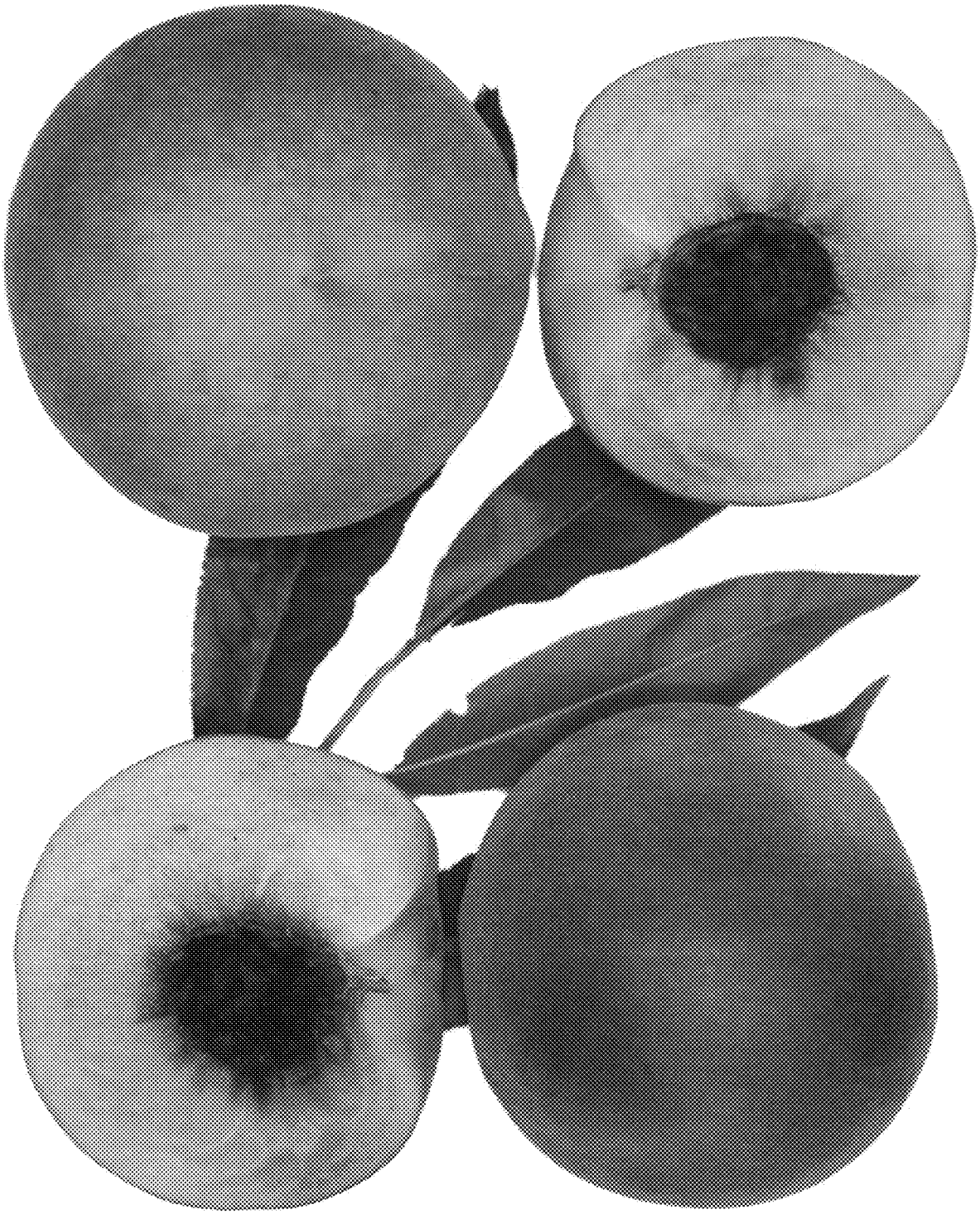

* * * * *